(12) United States Patent  (10) Patent No.: US 6,689,171 B2
Slemker et al.  (45) Date of Patent: *Feb. 10, 2004

(54) SHUTTLE LOCK

(75) Inventors: Tracy C. Slemker, Clayton, OH (US);
Scott R. Schall, Englewood, OH (US);
Steve Steinbarger, Centerville, OH (US)

(73) Assignee: Prosthetic Design, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 10/103,901

(22) Filed: Mar. 22, 2002

(65) Prior Publication Data

US 2002/0116071 A1 Aug. 22, 2002

Related U.S. Application Data

(63) Continuation of application No. 09/479,542, filed on Jan. 7, 2000, now Pat. No. 6,361,569.

(51) Int. Cl.[7] .................................................. A61F 2/60
(52) U.S. Cl. .......................................... 623/33; 623/38
(58) Field of Search .............................. 623/27, 32–38; 403/105, 152, DIG. 4; 602/23, 62, 63

(56) References Cited

U.S. PATENT DOCUMENTS

| 5,226,918 A | 7/1993 | Silagy et al. |
|---|---|---|
| 5,376,129 A | 12/1994 | Faulkner et al. |
| 5,507,837 A | 4/1996 | Laghi |
| 5,718,925 A | 2/1998 | Kristinsson et al. |
| 5,728,167 A | 3/1998 | Lohmann |
| 5,888,234 A | 3/1999 | Littig |
| 5,931,872 A | 8/1999 | Lohmann |
| 6,106,559 A | 8/2000 | Meyer |
| 6,361,569 B1 * | 3/2002 | Slemker et al. ............... 623/33 |
| 6,440,173 B1 | 8/2002 | Meyer |

OTHER PUBLICATIONS

Prosthetic Design, Inc. Product Catalog, pp. 9–11, Jun. 16, 1999.

* cited by examiner

Primary Examiner—Bruce E Snow
(74) Attorney, Agent, or Firm—Taft, Stettinius & Hollister LLP

(57) ABSTRACT

A shuttle-lock for maintaining a patient's residual limb in a prosthetic limb socket includes: (a) a housing having a distal surface adapted to abut an inside surface of a prosthetic limb socket, a substantially concave proximal surface and a hole extending into the center of the proximal surface, where the hole is adapted to receive a plunger pin carried on a patient's residual limb therein; and (b) a lock positioned within the housing for securing the plunger pin received in the hole where the concave proximal surface includes a plurality of radially extending grooves that are adapted to guide the plunger pin into the hole.

26 Claims, 6 Drawing Sheets

SHUTTLE LOCK

CROSS REFERENCE TO RELATED APPLICATIONS

This application is a continuation of U.S. patent application Ser. No. 09/479,542, filed Jan. 7, 2000, now U.S. Pat. No. 6,361,569.

BACKGROUND

The present invention relates to prosthetic devices, and more particularly, to a shuttle lock for securing a patient's residual limb in a prosthetic limb socket.

Conventional shuttle locks for securing a patient's residual limb in a prosthetic limb socket are typically disc-shaped and mounted within a distal end of the prosthetic limb socket. The shuffle locks typically include an axial hole extending therethrough and include a spring-loaded, reciprocating pawl cooperating with the axial hole to engage the sloping teeth of a ratcheted plunger pin extending from a distal end of a covering carried on the patient's residual limb. Accordingly, when the patient wishes to don the prosthetic limb, the patient will first don the covering onto his or her residual limb such that the plunger pin extends distally therefrom and will then insert the residual limb into the prosthetic limb socket such that the plunger pin is received within the axial hole of the shuttle lock and is secured therein by the spring-loaded pawl. Such shuttle locks will also include a release mechanism that removes the pawl from the axial hole of the shuttle lock so that the patient can disengage the plunger pin from the shuffle lock and thus remove his or her residual limb from the prosthetic limb socket.

Although most shuttle locks include a substantially concave proximal surface, where the axial hole centers at the bottom of the concavity, to facilitate locating the plunger pin into the center hole of the shuffle lock, it is sometimes a problem for the patients to locate the center hole of the shuttle lock while inserting his or her residual limb into the prosthetic limb socket. Another known problem is that for residual limbs having a more conical or cylindrical shape, the patient may experience undesirable rotation of the prosthetic limb socket with respect to his or her residual limb.

Yet another known disadvantage with conventional shuttle locks is that the design of the shuttle lock allows the plunger pin to "wiggle" within the axial hole, which leads to wear in the shuttle lock and prosthetic limb socket components. Since the shuttle lock is desirably low in profile (axial thickness) and since, in some cases, substantial radial clearance is provided between the outer diameter of the plunger pin and the inner diameter of the axial hole (to compensate for mis-aligned engagement), excess 'play' results in the plunger pin.

The proximal surface of the prosthetic limb socket and the distal surface of the shuttle lock abutting the proximal surface at the distal end of the prosthetic limb socket are typically designed to be perfectly flat such that when the shuttle lock is bolted into the distal end of the prosthetic limb socket, "binding" will not be experienced between the two abutting surfaces. However, if these two abutting surfaces are not totally flat and/or totally parallel, binding of the plastic shuttle lock may occur, which could lead to damage of the shuttle lock and/or the prosthetic limb socket.

Accordingly, a need exists for an improved shuttle lock which assists a patient in locating the axial hole of the shuttle lock with the plunger pin extending from his or her residual limb; a shuttle lock in which the plunger pin is stabilized within the axial hole when secured therein so as to reduce wear on the shuttle lock and/or prosthetic limb socket components; a shuttle lock which reduces the chances of binding between the abutting surfaces of the shuttle lock and prosthetic limb socket; and a shuttle lock that is easier to fabricate and maintain.

SUMMARY

One aspect of the present invention provides a shuttle lock for maintaining a patient's residual limb in a prosthetic limb socket, where the shuttle lock includes (a) a housing having a distal surface adapted to abut an inside surface of a prosthetic limb socket, a substantially concave proximal surface and a hole extending into the center of the proximal surface, where the hole is adapted to receive a plunger pin carried on a patient's residual limb; (b) a lock positioned within the housing for securing the plunger pin received in the axial hole; and (c) means for securing the housing of the shuttle lock within the prosthetic limb socket; (d) where the concave proximal surface includes at least one radial groove which is adapted to guide the plunger pin into the axial hole. Preferably the housing is substantially cylindrical in the concave proximal surface includes a plurality of the radial grooves circumferentially distributed thereabout, where the radial grooves extend substantially from and outer circumference of the concave proximal surface to an outer circumference of the axial hole. It is preferred that the lock involves a spring-loaded pawl positioned within the housing for engagement with a ratcheted plunger pin; however it is within the scope of the present invention to provide other forms of locks suitable for securing the plunger pin within the axial hole extending into the shuttle-lock housing, such as a magnetic lock, for example.

Another aspect of the present invention provides a shuttle lock for maintaining a patient's residual limb in a prosthetic limb socket that includes: (a) a housing having a distal surface adapted to abut an inside surface of a prosthetic limb socket, a hole extending axially therethrough and adapted to receive a plunger pin carried on a patient's residual limb; (b) a lock positioned within the housing for securing the plunger pin received in the axial hole; (c) means for securing the housing within a prosthetic limb socket; and (d) an annular protrusion extending distally from the distal opening of the axial hole, where the annular protrusion is coaxial with the axial hole and has an inner diameter substantially equal to the diameter of the axial hole so that the annular protrusion assists in stabilizing the plunger pin when received within the axial hole. Preferably, the protrusion extends through a hole in the prosthetic limb socket and has a height substantially equal to the thickness of the prosthetic limb socket material. Furthermore, it is preferred that the axial hole extending through the shuttle lock is provided by a hardened or metal bushing extending axially through the housing and distally from the housing to provide the annular protrusion. This bushing provides reinforcement to the shuttle lock and substantially reduces the amount of wear imparted by the plunger pin onto the shuttle lock components due to its hardness and wear characteristics.

Another aspect of the present invention provides a shuttle lock for maintaining the patient's residual limb in a prosthetic limb socket that includes: (a) a housing having a distal surface, a substantially concave proximal surface and a hole extending into the center of the proximal surface which is adapted to receive a plunger pin carried on a patient's residual limb; (b) a lock positioned within the housing for securing the plunger pin received in the axial hole; (c) a plurality of holes or bores extending into the distal surface of the housing for receiving a corresponding plurality of bolts or screws which are used to secure the housing within the prosthetic limb socket; and (d) at least one projection extending from the distal surface of the housing, where the projection is adapted to abut an inside surface of the prosthetic limb socket and assume the majority of the load distribution when the shuttle lock is secured in the prosthetic limb socket. By reducing the load distribution on the distal surface of the housing, the projection thereby substantially reduces "binding" between the distal surface of the housing and the inside surface of the prosthetic limb socket. Preferably, the distal surface of the housing is substantially flat and the projection has a substantially flat distal surface on a plane parallel to the distal surface of the housing. It is also preferred that there are a plurality of projections, where each projection is substantially annular and surrounds a respective one of the bores, and that the projections extend distally for a distance equal to approximately 0.001 to 0.020 inches.

Another aspect of the present invention provides a shuttle lock for maintaining a patent's residual limb in a prosthetic limb socket that includes: (a) an upper housing plate having a substantially concave proximal surface, a distal end and an axial hole extending completely therethrough, into the center of the substantially concave proximal surface and out through the distal end; (b) a lower housing plate having a proximal end removably coupled to the distal end of the upper housing plate, a distal surface adapted to abut an inside surface of a prosthetic limb socket and an axial hole extending into the proximal end, coaxial with the axial hole extending through the upper housing plate and adapted to receive a ratcheted plunger pin carried on a patient's residual limb; (c) a spring-loaded pawl, mounted within the lower housing plate for reciprocation radially into and out from the axial hole extending into the lower housing plate, and adapted to engage the plunger pin received in the axial hole; and (d) means for securing the lower housing plate within the prosthetic limb socket. Preferably, the distal end of the upper housing plate and the proximal end of the lower housing plate are substantially flat.

It is also preferred that the shuttle lock includes: (e) a push rod slidably received within the lower housing plate; (f) a lever, mounted to the lower housing plate, operatively coupled between the push rod and the pawl such that movement of the push rod to a first position causes the pawl to reciprocate at least partially into the axial hole and movement of the push rod to a second position causes the pawl to reciprocate out from the axial hole; and (g) a spring biasing the push rod to the first position. Preferably, the pawl is slidingly positioned in a first radial hole extending into an outer circumferential surface of the lower housing plate and out through the axial hole extending into the lower housing plate, the push rod is slidably positioned in a second radial hole extending into the outer circumferential surface of the lower housing plate, the lever is pivotably mounted to the flat proximal surface of the lower housing plate; and the shuttle lock further comprises a first pin extending from the first end of the lever, through an opening in the flat proximal surface of the lower housing plate and into the push rod, and a second pin extending from a second end of the lever, through an opening in the flat proximal surface of the lower housing plate and into the pawl. This second pin extending through a proximal surface of the lever is preferably slidingly removable from the lever and pawl so as to facilitate simple replacement of the pawl in the lower housing plate. Because the pawl is slidingly received in the first radial hole, once the second pin is removed, the pawl can be slid out from the lower housing plate and replaced if damaged or worn.

Another aspect of the present invention provides a prosthetic limb that includes: (a) a covering adapted to be worn on a patient's residual limb, where the covering includes a plunger pin extending from a distal end of the covering; (b) a prosthetic limb socket adapted to receive the patient's residual limb with the covering worn thereon; and (c) a shuttle lock mounted within the prosthetic limb socket, at a distal end of the prosthetic limb socket, where the shuttle lock includes a substantially concave proximal surface, a hole extending into the center of the proximal surface for receiving the plunger pin, and a lock for securing the plunger pin within the axial hole. The proximal surface of the shuttle lock includes at least one radial groove and the covering preferably includes a projection extending distally therefrom which is adapted to be received within the radial groove on the proximal surface of the shuttle lock so as to reduce rotation of the patient's residual limb and covering with respect to the prosthetic limb socket when the plunger pin is secured within the axial hole of the shuttle lock. Preferably, the concave proximal surface of the shuttle lock includes a plurality of radial grooves circumferentially distributed thereabout and the covering includes a plurality of ribs extending distally therefrom and oriented radially with respect to the plunger pin, so that the ribs are adapted to be received within the radial grooves to provide the anti-rotation discussed above.

Accordingly, it is an object of the present invention to provide a shuttle lock adapted to assist a patient in donning a prosthetic limb socket, and specifically, a shuttle lock that assists the patient in locating the axial hole extending through the shuttle lock with the plunger pin extending distally from the covering worn on the patient's residual limb. It is a further object of the present invention to provide a shuttle lock that is less susceptible to wear, and a shuttle lock that is designed to reduce binding between the shuttle lock housing and the prosthetic limb socket. It is a further object of the present invention to provide a prosthetic limb that is designed to reduce undesirable rotation between the patient's residual limb with respect to the prosthetic limb socket. Finally, it is an object of the present invention to provide a shuttle lock that is relatively uncomplicated and inexpensive to manufacture; and that is relatively easy to maintain. These and other objects and advantages of the present invention will be apparent from the following description, the attached drawings and the appended claims.

DETAILED DESCRIPTION

Figure 1:
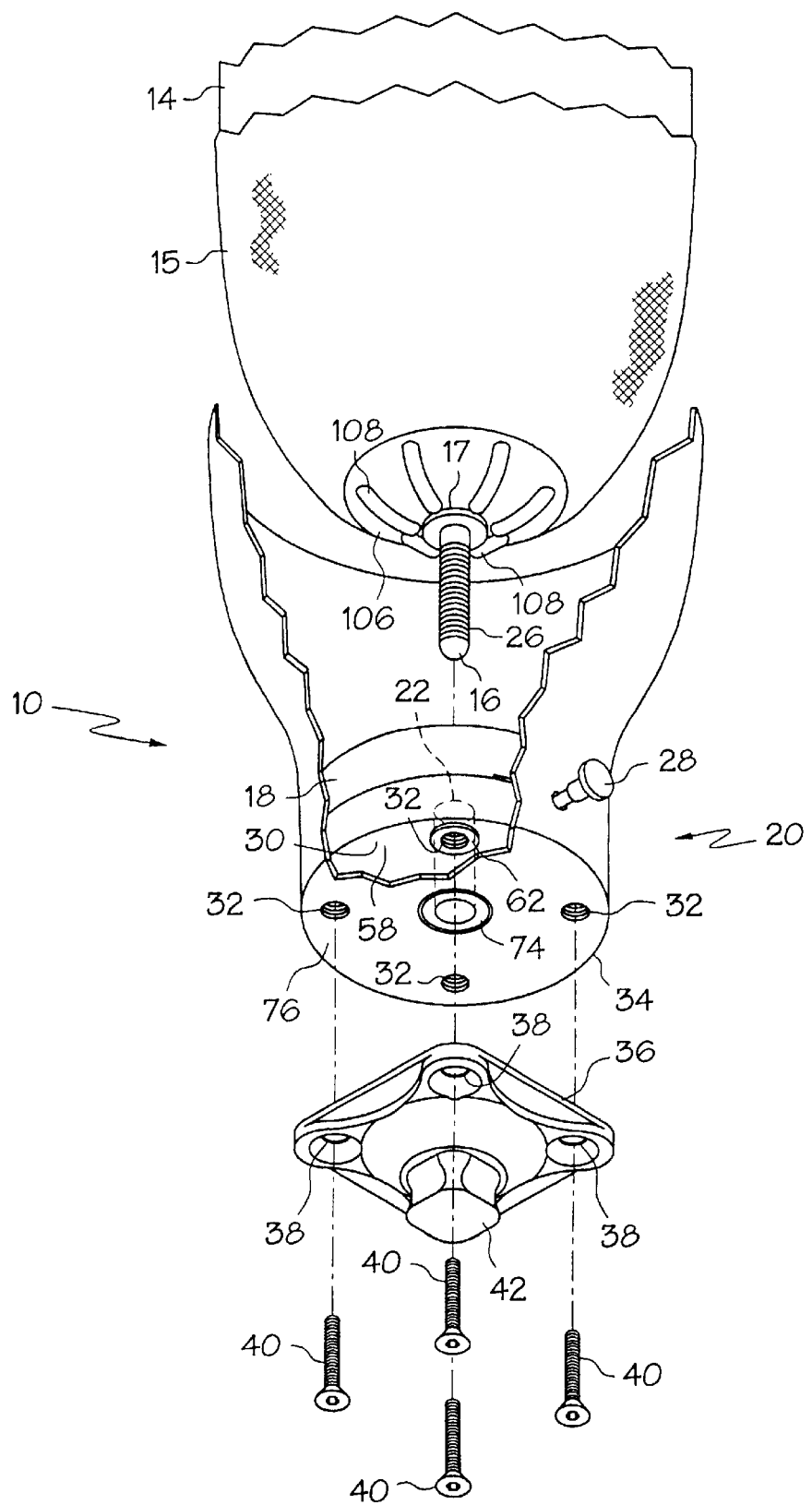
FIG. 1 is an exploded, perspective view of a prosthetic limb including the shuttle lock and residual limb covering of the preferred embodiment of the present invention.

As shown in FIG. 1, a socket assembly 10 of a prosthetic limb in accordance with the present invention will include a hard plastic outer socket 12, and, preferably, a covering that includes a soft and resilient suspension sleeve 14 rolled onto the patient's residual limb, surrounded by a knitted sock 15. The suspension sleeve is formed to snugly fit over the residual limb of the patient and to provide comfort to the residual limb of the patient when the prosthetic limb is worn by the patient. The suspension sleeve 14 has a plunger pin 16 extending distally from a distal end of the suspension sleeve, and the sock 15 includes a hole 17 that allows the plunger pin 16 to extend therethrough. The plunger pin 16 is adapted to engage with and lock within a shuttle lock 18 releasably mounted within an extended portion 20 of the outer socket 12. The preferred embodiment of the shuttle lock 18 includes an axial channel or hole 22 extending axially therethrough for receiving and securing the plunger pin 16 therein. A spring loaded pawl 24 (see FIGS. 2, 4, 7A, 7B, 8A and 8B) extending within the axial hole 22 engages with teeth 26 of the ratcheted plunger pin 16 such that the pawl 24 and the shape of the teeth 26 allow the locking pin to be easily inserted within the axial hole, yet prohibit the locking pin from being extracted again from the axial hole 22. A spring loaded push rod 28 may be pressed by the patient to disengage the pawl 24 extending within the axial hole 22 from the teeth 26, thereby allowing the plunger pin 16 to be extracted again from the axial hole. The spring loaded release and locking mechanisms will be described in greater detail below.

The outer socket 12 is typically created by heating a thermoplastic "preform" cone until it is sufficiently soft and flexible, stretching the heated cone over a positive cast of the amputee's residual limb, and then vacuum forming the cone in place over the positive cast. Alternatively, the outer socket can be fabricated by heating an extruded sheet of thermoplastic material and wrapping the sheet over the positive cast; or by a laminating process using a fiber reinforced, thermoset plastic. The distal end of the positive cast preferably includes an extended portion or a blank attached thereto to provide for the dimensions of the shuttle lock 18. Therefore, when the heated cone is stretched over this modified positive cast, the extended portion 20 of the outer socket will be created. The suspension sleeve 14 is typically formed from a pliable, silicone material and includes the plunger pin 16 and associated support flange (not shown) molded therein. An example of a suspension sleeve suitable for use with the present invention includes an "Alpha" locking liner, commercially available from Ohio Willowood Co.

The distal end 30 of the shuttle lock 18 has four threaded holes 32 which are aligned with four holes extending through the distal end 34 of the outer socket 12. A conventional pyramid plate 36 includes four holes 38 which are to be aligned with the four threaded holes 32 of the shuttle lock 18. Accordingly, four threaded screws or bolts 40 are used to attach the pyramid plate 36 to the distal end 34 of the outer socket and simultaneously secure the shuttle lock 18 within the extended portion 20 of the outer socket. As is known to those of ordinary skill, a pyramidal boss 42 formed integrally with the pyramid plate 36 is provided to attach an upright assembly (not shown) of the prosthetic limb to the distal end of the prosthetic limb socket assembly 10.

Figure 2:
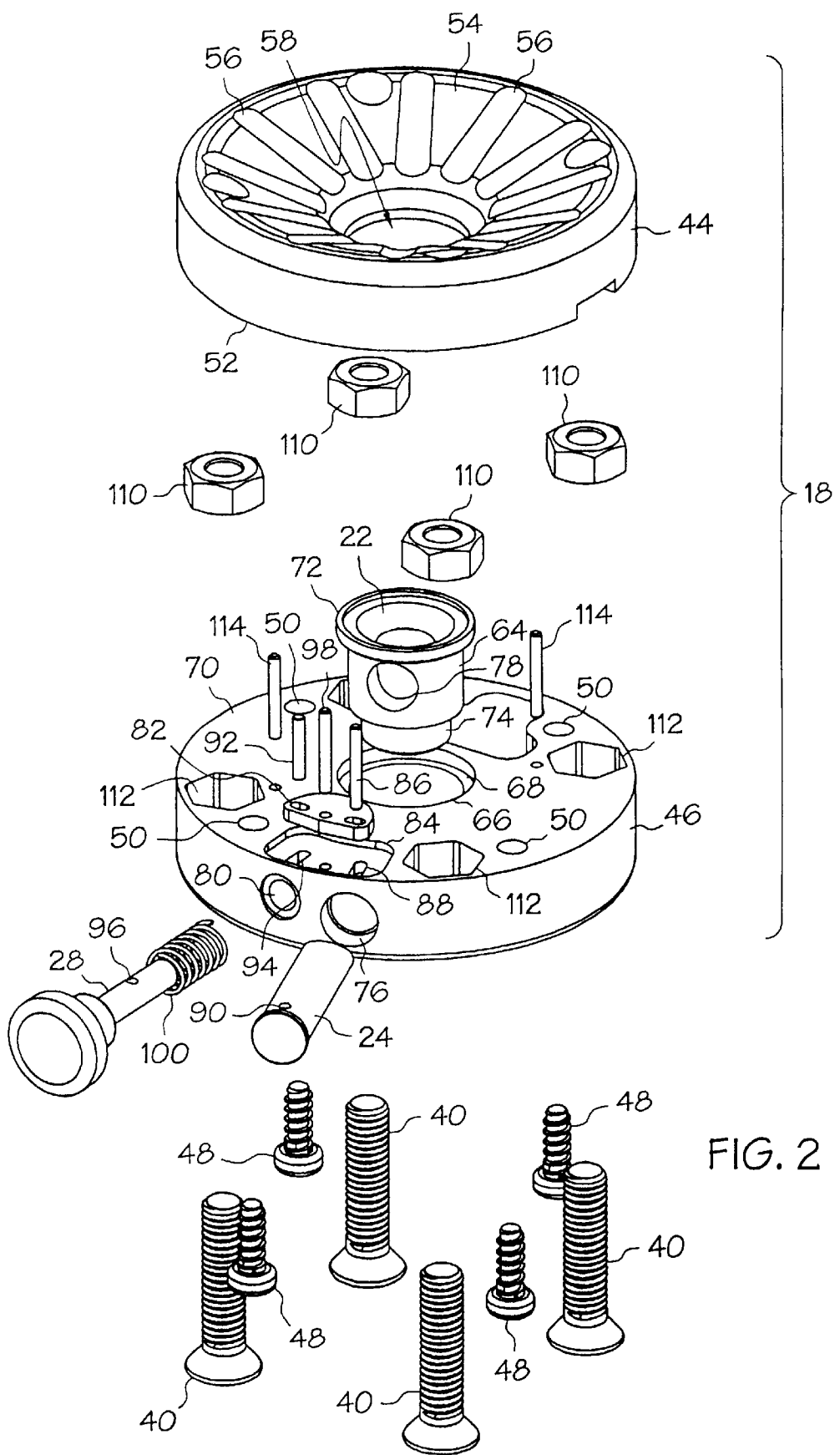
FIG. 2 is an exploded, perspective view of the preferred embodiment of the shuttle lock.
Figure 3:
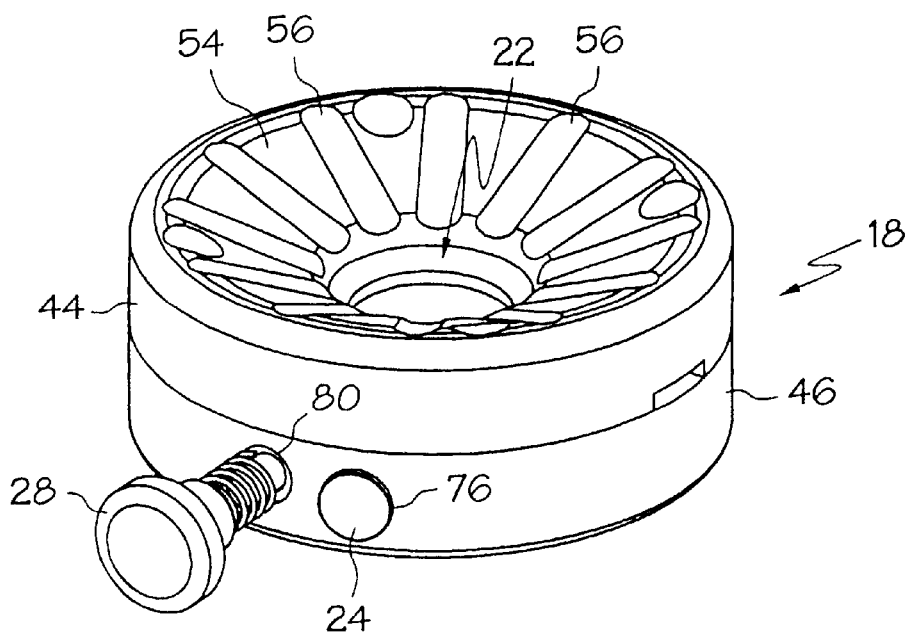
FIG. 3 is a perspective view of the preferred embodiment of the shuttle lock.
Figure 4:
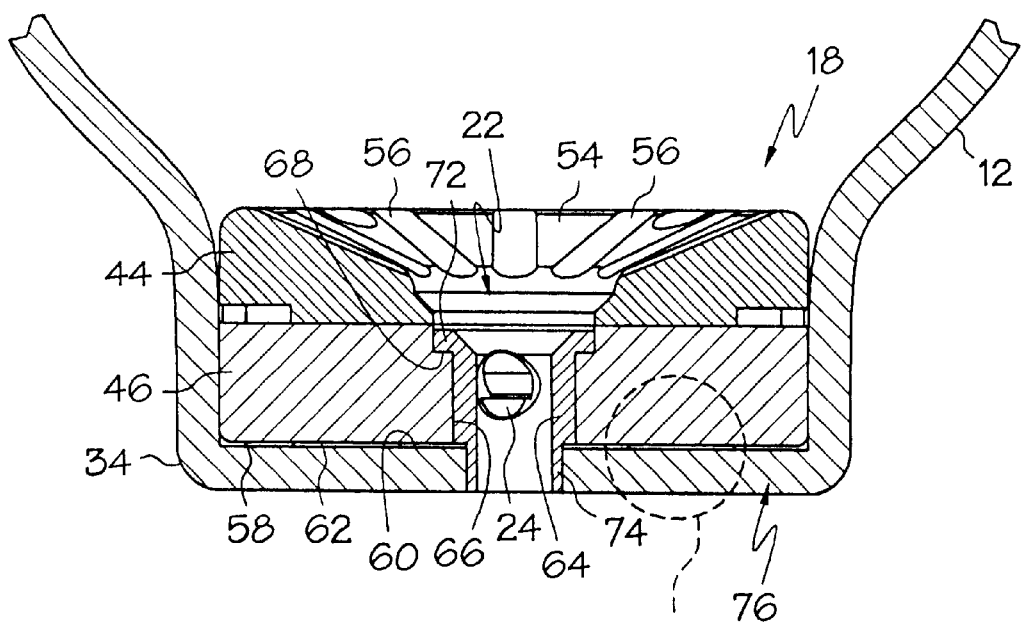
FIG. 4 is a cross-sectional view of the preferred embodiment of the shuttle lock mounted within a prosthetic limb socket.

As shown in FIGS. 2, 3 and 4, the preferred embodiment of the shuttle lock 18 includes a disc shaped, upper housing plate 44 and a disc shaped, lower housing plate 46, removably connected together by a plurality of screws 48 extending upward through holes 50 in the lower housing plate and threaded into holes (not shown) in the flat distal surface 52 of the upper housing plate 44. The upper housing plate 44 has a substantially concave proximal surface 54 and includes a plurality of grooves 56 extending radially, substantially from an outer circumference of the plate 44 to an outer circumference of the central hole 58 in the upper housing plate 44. The central hole 58 opens to the axial hole 22 when the upper and lower housing plates are connected together. The radial grooves 56 are evenly distributed circumferentially thereabout and act to assist the patient in guiding the plunger pin 26 from the substantially concave proximal surface 54 to the axial hole 22. For example, when the patient inserts the plunger pin 26 carried on his or her residual limb into the socket 12, it is sometimes difficult to locate the center hole 22 and the plunger pin 26 will first contact the concave proximal surface 54, and slide around thereon. When the plunger pin slides into one of the grooves 56, the shape of the grooves will likely prevent the plunger pin from sliding out again and distal pressure on the plunger pin will cause it to slide radially within the groove 56 towards the axial hole 22 until it is received therein. As will be discussed in further detail below, the radial grooves 56 may also cooperate with ribs extending from the suspension sleeve to substantially limit rotation of the patient's prosthetic limb with respect to the outer socket 12.

The upper and lower housing plates 44, 46 are preferably molded from a rigid plastic material such as DELRIN. However, it is within the scope of the present invention that the upper and lower housing plates 44, 46 may also be made from other suitable, rigid materials such as nylon, aluminum, steel, etc.

Figure 5:
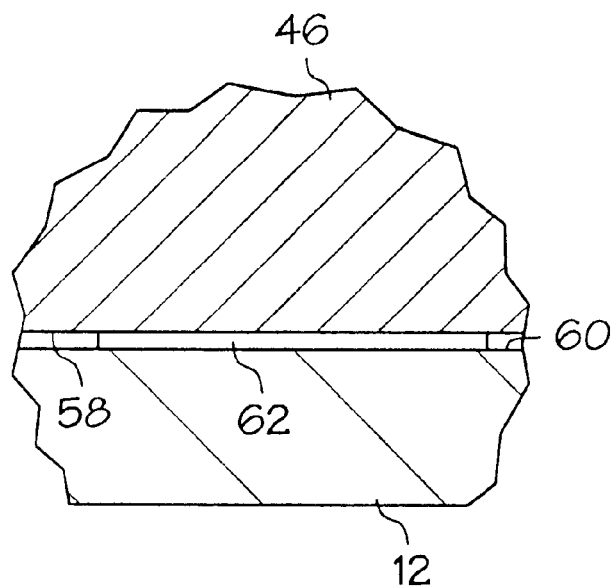
FIG. 5 is a magnified view of the area indicated as "5" in FIG. 4.

As shown primarily in FIGS. 1, 4 and 5, the distal surface 58 of the lower housing plate 46 is substantially flat and designed to lie on a plane parallel to the flat proximal inner surface 60 at the distal end 34 of the outer socket 12. The parallel orientation of the two surfaces 58, 60 substantially prevents binding (or twisting) of the shuttle lock 18 with respect to the socket 12 when the bolts 40 are tightened. However, because it is very difficult to ensure that both surfaces 58, 60 are perfectly parallel, a plurality of annular projections 62 and provided on the distal surface 58 of the lower housing plate 46 to reduce surface area contact between the lower housing plate 46 and the proximal inner surface 60 at the distal end of the prosthetic limb socket. Preferably, four of such annular projections 62 are provided, where each of the annular projections 62 encircle the threaded holes 32 extending into the distal surface 58 of the lower housing plate 46. In the preferred embodiment, the projections are 0.012 inches high, but it is within the scope of the invention to provide 0.0001 to 0.020 inch high projections. These projections 62 are adapted to assume the majority of the clamping force between the housing of the shuttle lock 18 and the prosthetic limb socket 12 when the housing is secured within the prosthetic limb socket by the bolts 40, thereby substantially reducing "binding" between distal outer surface 58 of the housing and the proximal inner surface 60 of the prosthetic limb socket.

As shown primarily in FIGS. 1, 2 and 4, the lower housing plate 46 also preferably includes a hardened bushing 64 received within a hole 66 extending axially through the center of the lower housing plate 46. The bushing 64 is preferably made from Bronze 660, however other metals or hardened materials are also suitable for the present invention. The inner diameter of the bushing 64 provides the axial hole 22 for receiving the plunger pin 26 therein. The hole 66 includes a shoulder 68 extending radially inwardly from the proximal surface 70 of the lower housing plate 46 that engages an outwardly extending flange 72 of the bushing 64, which maintains the bushing 64 within the hole 66. The bushing 64 also includes a portion 74 that extends axially therefrom in a distal direction to protrude distally from the distal surface 58 of the lower housing plate 46. This protrusion 74 preferably extends a distance equal to the thickness of the outer socket 12 (plus the height of the projections 62) so that the protrusion 74 does not extend distally from the distal surface 76 of the outer socket 12. This bushing 64 provides a reinforcing surface to the axial hole 22, thus minimizing wear caused by the plunger pin 26 and the protrusion 74 extends the axial hole distally for the thickness of the outer socket 12 to provide a further level of stabilization to the plunger pin when received within the axial hole 22, while not adding any profile to the shuttle lock 18.

In an alternate embodiment, the bushing 64 is not used, and the volume of the lower housing plate 44 formerly taken by the bushing 64 (including the protrusion 74) is taken by the material of the lower housing plate, integrally formed together. While such an alternate embodiment does not provide the wear resistance of the metal bushing 64, the protrusion extending from the distal end of the lower housing plate still reduces excessive wear by reducing "wiggle" in the plunger pin. This alternate embodiment is also less expensive to produce.

Figure 6:
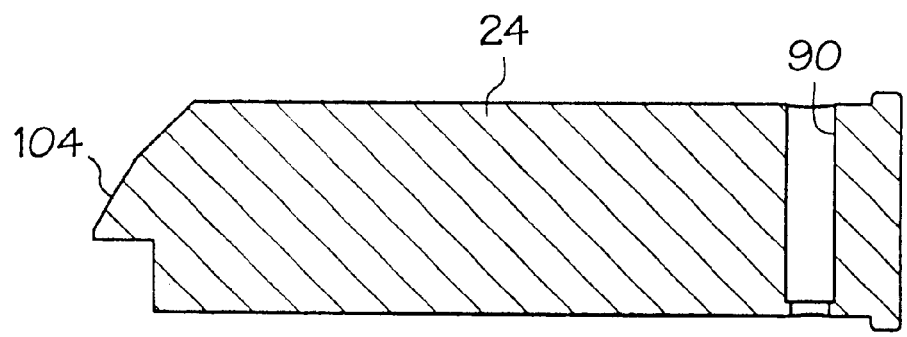
FIG. 6 is a cross-sectional view of the pawl for use with the preferred embodiment of the shuttle lock.

As shown primarily in FIGS. 2, 3, 7A and 8A, the pawl 24 is positioned to reciprocate within a radial channel 76 extending radially into the outer circumferential surface of the lower housing plate 46 into the hole 68. A radial hole 78 extends through the side of the bushing 64 to allow the pawl 24 to extend into and out from the axial hole 22 provided by the bushing 64. The push rod 28 is also positioned for reciprocation in a radial channel 80 extending radially into the outer circumferential surface of the lower housing plate 46. The radial channels 76, 80 are separated radially from one another at an angle of approximately 19°. A lever 82 is seated in a depression 84 formed into the flat proximal surface 70 of the lower housing plate 46. A first end of the lever is coupled to the pawl 24 by a pin 86 extending axially through the lever 82, through a groove 88 extending axially through the flat proximal surface 70 of the lower housing plate 46, into the radial channel 76 and into a slot 90 (see FIG. 6) extending into the pawl 24. The lever 82 is pivotly coupled to the push rod by another pin 92, which extends through one end of the lever, through a second groove 94 extending axially through the flat proximal surface 70 of the lower housing plate 46, into the radial channel 80 and into a slot 96 extending into the push rod 28. A pivot pin 98 pivotally couples the lever 82 to the depression 84 formed into the flat proximal surface 70 of the lower housing plate 46. Grooves 88 & 94 allow pins 86 & 92, respectively, to travel radially in the lower housing plate 46 during pivoting of the lever 82.

Figure 7A:
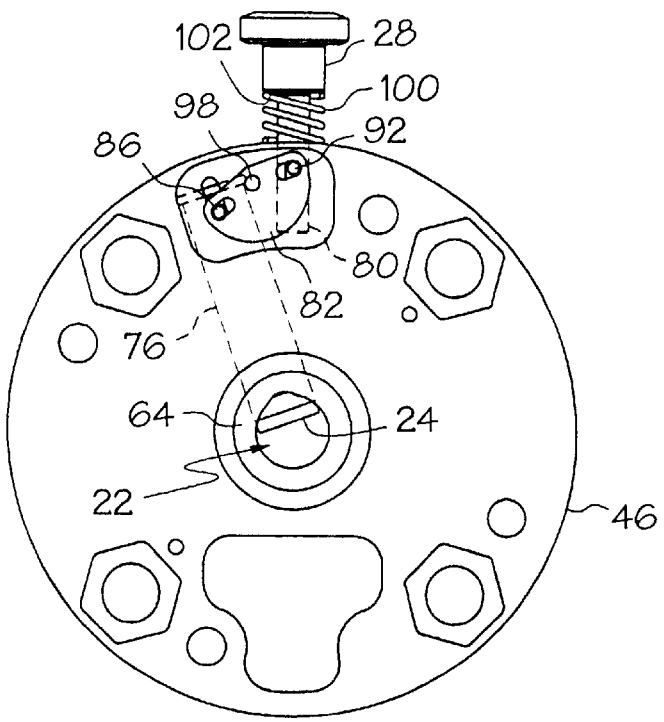
FIG. 7A is a top plan view of the lower housing plate of the preferred embodiment of the shuttle lock showing the lock components in a "locking" position.
Figure 7B:
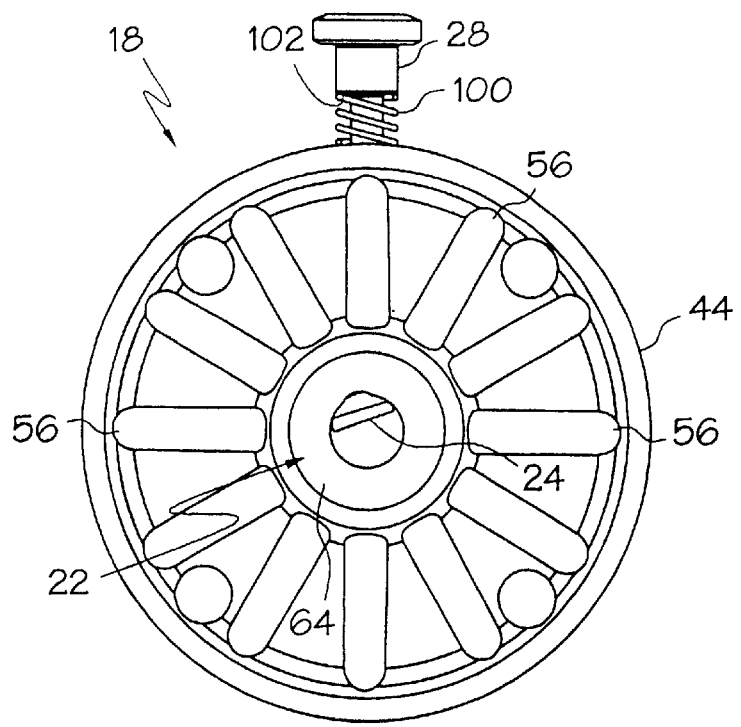
FIG. 7B is a top plan view of the preferred embodiment of the shuttle lock showing the lock components in a "locking" position.

As shown in FIGS. 7A and 7B, a spring 100 is positioned on the push rod 28 between the outer circumferential surface of the lower housing plate 46 and a flange 102 extending from the push rod to bias the push rod 28 radially outwardly, which causes the lever 82 to pivot counterclockwise on the pivot pin 98, which in turn causes the pawl 24 to be pushed radially inwardly so that at least the tapered edge 104 of the pawl extends into the axial hole 22. In this position of the pawl 24, the shuttle lock is in a "locking" position.

Figure 8A:
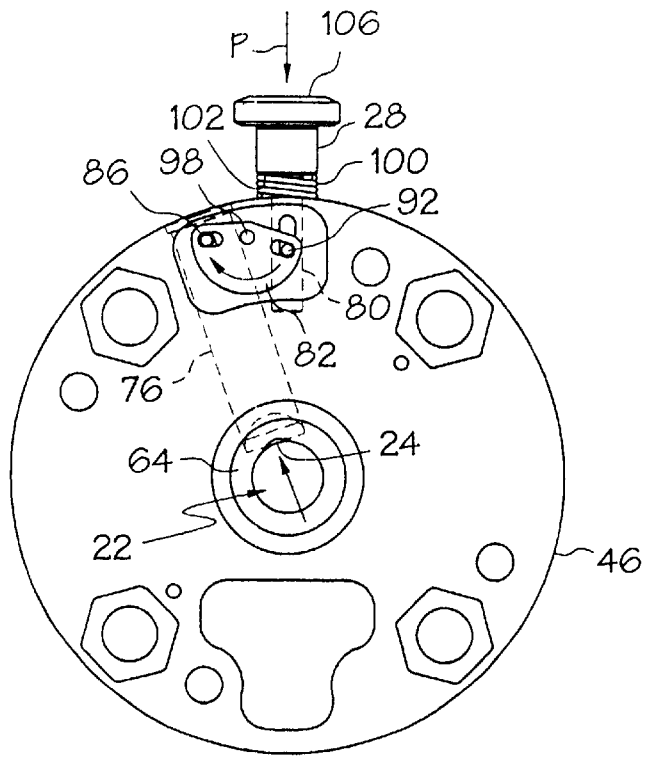
FIG. 8A is a top plan view of the lower housing plate of the preferred embodiment of the shuttle lock showing the lock components in a "unlocked" position.
Figure 8B:
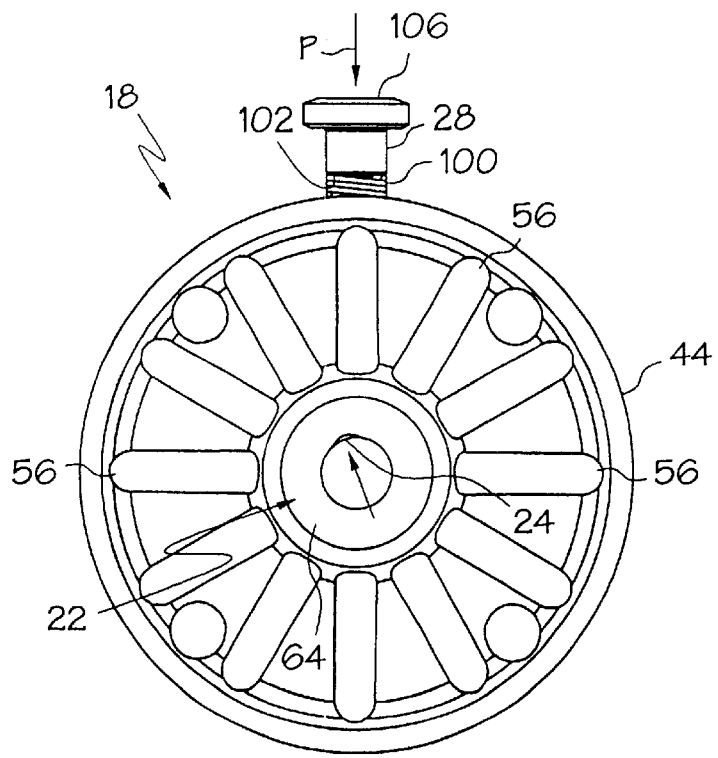
FIG. 8B is a top plan view of the preferred embodiment of the shuttle lock showing the lock components in the "unlocked" orientation.

As shown in FIGS. 8A and 8B, by applying radial pressure (shown by arrow P) to the radial end 106 of the push rod 28, the lever 82 will be caused to rotate clockwise, which in turn forces the pawl 24 to withdraw radially from the axial hole 22, thus releasing the plunger pin 16 (if present within the axial hole 22).

Because at least the pin 86 is easily removed from the assembly, the pawl 24 may be easily removed, inspected and/or replaced by removing the pin 86 and sliding out the pawl 24 from the radial channel 76. A new pawl 24 may be inserted into the radial channel 76 and the pin may be reinserted to secure the pawl 24 back again within the radial channel 76.

As shown in FIG. 1, the knitted sock 15 includes a cap 106 formed onto or bonded to its distal end, where the plunger ping 16 extends distally through the center of the cap 106. The cap 106 includes a plurality of projections extending distally therefrom in the form of radial ribs 108, evenly spaced circumferentially thereabout. The cap 106 and ribs 108 are preferably formed from a rubber or rubber-like material that acts to grip the hard plastic material of the shuttle lock housing. The ribs 108 are adapted to be received in the radial grooves 56 present in the concave proximal surface 54 of the shuttle lock housing, thereby limiting the amount of undesirable rotation experienced by the patient's residual limb with respect to the prosthetic limb socket 12.

Referring to FIG. 2, the threaded holes 32 in the distal end of the shuttle lock 18 are provided by nuts 110 respectively seated in hexagonal depressions 112 extending into the proximal surface 70 of the lower housing plate 46. Pins 114 are used to help secure the upper 20 and lower housing plates 44, 46 together without rotation with respect to each other.

Having described the invention in detail and by reference to preferred embodiments thereof, it will be apparent that modifications and variations are possible without departing from the scope of the invention as defined by the following claims.

What is claimed is:

1. A shuttle-lock for maintaining a patient's residual limb in a prosthetic limb socket, the shuttle-lock comprising:
   a housing having a distal surface adapted to abut an inside surface of a prosthetic limb socket, a substantially concave proximal surface and a hole extending into the center of the proximal surface, the hole being adapted to receive a plunger pin carried on a patient's residual limb therein;
   a lock positioned within the housing for securing the plunger pin received in the hole; and
   means for securing the housing within a prosthetic limb socket;
   the housing being substantially cylindrical and the concave proximal surface including a plurality of radially extending grooves, being circumferentially distributed about the hole and providing an unobstructed path for the plunger pin to be received within a groove of the plurality of radially extending grooves and guided directly into the hole.

2. The shuttle-lock of claim 1, wherein the radially extending grooves extend radially out from an outer circumference of the hole.

3. A shuttle-lock for maintaining a patient's residual limb in a prosthetic limb socket, the shuttle-lock comprising:
a housing having a distal surface adapted to abut an inside surface of a prosthetic limb socket, a proximal surface and a hole extending completely therethrough into a proximal opening in the proximal surface and out through a distal opening in the distal surface, the hole having a diameter and being adapted to receive a plunger pin carried on a patient's residual limb therein;
a lock positioned within the housing for securing the plunger pin received in the hole; and
means for securing the housing within a prosthetic limb socket; and
a tubular protrusion extending distally from the distal opening of the hole, the tubular protrusion being coaxial with the hole and having an inner diameter substantially equal to the diameter of the hole and having an outer cylindrical surface, whereby the tubular protrusion assists in stabilizing the plunger pin when received within the hole.

4. The shuttle-lock of claim 3, wherein the protrusion extends distally for a distance approximately equal to a thickness of the prosthetic limb socket.

5. The shuttle-lock of claim 4, further comprising a hardened bushing mounted within the housing and providing the hole, the bushing extending distally from the housing to provide the tubular protrusion.

6. A shuttle-lock for maintaining a patient's residual limb in a prosthetic limb socket, the shuttle-lock comprising:
an upper housing plate having a substantially concave proximal surface, a distal end and an axial hole extending completely therethrough, into the center of the substantially concave proximal surface and out through the distal end;
a lower housing plate having a proximal end removably coupled to the distal end of the upper housing plate, a distal surface adapted to abut an inside surface of a prosthetic limb socket and an axial hole extending into the proximal end, coaxial with the axial hole extending through the upper housing plate and adapted to receive a ratcheted plunger pin carried on a patient's residual limb;
a spring-loaded pawl, mounted within the lower housing plate for reciprocation radially into and out from the axial hole extending into the lower housing plate, and adapted to engage the ratcheted plunger pin received in the hole; and
a release mechanism mounted between the proximal end and the distal end of the lower housing plate operatively coupled to the spring-loaded pawl to reciprocate the spring-loaded pawl out from the axial hole when activated.

7. A shuttle-lock for maintaining a patient's residual limb in a prosthetic limb socket, the shuttle-lock comprising:
an upper housing plate having a substantially concave proximal surface, a distal end and an axial hole extending completely therethrough, into the center of the substantially concave proximal surface and out through the distal end;
a lower housing plate having a proximal end removably coupled to the distal end of the upper housing plate, a distal surface adapted to abut an inside surface of a prosthetic limb socket and an axial hole extending into the proximal end, coaxial with the axial hole extending through the upper housing plate and adapted to receive a ratcheted plunger pin carried on a patient's residual limb;
a spring-loaded pawl, mounted within the lower housing plate for reciprocation radially into and out from the axial hole extending into the lower housing plate, and adapted to engage the ratcheted plunger pin received in the hole; and
a release mechanism mounted within the lower housing plate operatively coupled to the spring-loaded pawl to reciprocate the spring-loaded pawl out from the axial hole when activated;
the distal end of the upper housing plate and the proximal end of the lower housing plate are substantially flat.

8. The shuttle-lock of claim 7, further comprising:
a push rod slidably received within the lower housing plate;
a lever, mounted to the lower housing plate, operatively coupled between the push rod and the spring-loaded pawl such that movement of the push rod to a first position causes the spring-loaded pawl to reciprocate at least partially into the axial hole extending into the lower housing plate and movement of the push rod to a second position causes the spring-loaded pawl to reciprocate out from the hole extending into the lower housing plate; and
a spring biasing the push rod to the first position.

9. The shuttle-lock of claim 8, wherein:
the spring-loaded pawl is slidingly positioned in a first radial hole extending into an outer circumferential surface of the lower housing plate and out through the axial hole extending into the lower housing plate;
the push rod is slidingly positioned in a second radial hole extending into the outer circumferential surface of the lower housing plate;
the lever is pivotably mounted to the flat proximal surface of the lower housing plate, having a first end positioned over the push rod and a second end positioned over the spring-loaded pawl; and
the shuttle-lock further comprises a first pin extending from the first end of the lever, through an opening in the flat proximal surface of the lower housing and into the push rod, and a second pin extending from the second end of the lever, through an opening in the flat proximal surface of the lower housing and into the spring-loaded pawl.

10. The shuttle-lock of claim 9, wherein the second pin extends through the proximal surface of the lever and is slidingly removable from the lever and the spring-loaded pawl so as to facilitate simple replacement of the spring-loaded pawl in the lower housing plate.

11. A prosthetic limb comprising:
a covering adapted to be worn on a patient's residual limb, the covering including a plunger pin extending from a distal end thereof;
a prosthetic limb socket adapted to receive the patient's residual limb with the covering worn thereon; and
a shuttle-lock mounted within the prosthetic limb socket, at a distal end of the prosthetic limb socket, the shuttle-lock including a substantially concave proximal surface, a hole extending into the center of the proximal surface for receiving the plunger pin, and a lock for securing the plunger pin within the hole;
the proximal surface of the shuttle-lock further including a plurality of radially extending grooves being circumferentially distributed about the hole and providing an unobstructed path for the plunger pin to be received within a groove of the plurality of radially extending grooves and guided directly into the hole.

12. A prosthetic limb comprising:
a covering adapted to be worn on a patient's residual limb, the covering including a plunger pin extending from a distal end thereof;
a prosthetic limb socket adapted to receive the patient's residual limb with the covering worn thereon; and
a shuttle-lock mounted within the prosthetic limb socket, at a distal end of the prosthetic limb socket, the shuttle-lock including a substantially concave proximal surface, a hole extending into the center of the proximal surface for receiving the plunger pin, and a lock for securing the plunger pin within the hole;
the proximal surface of the shuttle-lock further including a plurality of radially extending grooves circumferentially distributed thereabout and adapted to guide the plunger pin into the hole; and
the covering further includes a projection extending distally therefrom, and the projection is adapted to be received within at least one of the plurality of radially extending grooves on the proximal surface of the shuttle-lock so as to reduce rotation of the patient's residual limb and covering with respect to the prosthetic limb socket when the plunger pin is secured within the hole of the shuttle-lock.

13. The prosthetic limb of claim 12, wherein the covering includes a plurality of ribs extending distally therefrom and oriented radially with respect to the plunger pin, the ribs being adapted to be received within the radially extending grooves.

14. The prosthetic limb of claim 12, wherein the projection is formed from a rubber-like material.

15. A shuttle-lock for maintaining a patient's residual limb in a prosthetic limb socket, the shuttle-lock comprising:
a housing having a substantially concave proximal surface and a hole extending into the center of the proximal surface, the hole being adapted to receive a male coupling carried on a patient's residual limb therein; and
a lock positioned within the housing for securing the male coupling received in the hole;
the concave proximal surface including at least one radially extending groove providing an unobstructed path for the male coupling to be received within the at least one radially extending groove and guided directly into the hole.

16. The shuttle-lock of claim 15, wherein the housing is substantially cylindrical and the concave proximal surface includes a plurality of the radially extending grooves circumferentially distributed thereabout.

17. The shuttle-lock of claim 16, wherein the radially extending grooves extend radially outwardly from an outer circumference of the hole.

18. A locking liner cap comprising:
a cap body having a convex distal surface;
a coupling provided on the convex distal surface adapted to lock the cap body within a distal end of a prosthetic limb socket; and
the convex distal surface having a plurality of distally extending projections set radially apart from a plunger pin or coupling and adapted to mate with a plurality of depressions provided within the distal end of the prosthetic limb socket.

19. A prosthetic sleeve adapted to be worn on a patient's residual limb and adapted to secure the patient's residual limb to a lock within a socket component of a prosthetic limb assembly, comprising:
a sleeve having an open proximal end for receiving a patient's residual limb and a substantially closed distal end; one of,
(i) a plunger pin extending from the distal end of the sleeve, and
(ii) a coupling positioned at the distal end of the sleeve for mounting the plunger pin thereto; and
at least one distally extending projection positioned on the distal end of the sleeve and set radially apart from the one plunger pin or coupling, the projection being adapted to mate with at least one depression provided on a distal surface of a lock provided within a socket component of a prosthetic limb assembly, to thereby limit rotation of the patient's residual limb with respect to the socket component.

20. The prosthetic sleeve of claim 19, wherein the coupling has a plurality of the projections positioned on the distal end of the sleeve adapted to mate with a plurality of depressions provided on the distal surface of the lock.

21. The prosthetic sleeve of claim 19, wherein the sleeve is one of a knitted sock and silicone liner.

22. The prosthetic sleeve of claim 20, wherein the plurality of projections are a plurality of radially extending ribs adapted to mate with a plurality of radially extending grooves provided on the distal surface of the lock.

23. A prosthetic limb comprising:
a substantially rigid outer socket including an open proximal end opening onto a limb-receiving chamber, and including a distal end having a distal end wall and a cylindrical channel extending through the distal end wall, the cylindrical channel having an inner diameter, the outer socket being adapted to receive and support a patient's residual limb therein and being adapted to be coupled to prosthetic limb upright components so that the prosthetic limb upright components will extend distally from an outer surface of the distal end wall; and
a shuttle-lock positioned within the limb-receiving chamber of the outer socket at the distal end of the outer socket, the shuttle-lock including a housing, the housing being removable from the limb-receiving chamber and having a distal end surface abutting a proximal surface of the distal end wall of the outer socket, a proximal surface, and a hole extending completely therethrough from a proximal opening in the proximal surface of the housing and out through a distal opening in the distal end surface of the housing, the hole having a diameter and being adapted to receive a plunger pin carried on the patient's residual limb therein, the shuttle-lock further including,
a lock positioned within the housing, and
a tubular extension, coaxial with the hole, extending distally from the distal opening of the hole and into the cylindrical channel in the distal end wall of the outer socket.

24. A shuttle-lock for maintaining a patient's residual limb in a prosthetic limb socket, the shuttle-lock comprising:
a housing having a distal surface adapted to abut an inside surface of a prosthetic limb socket, a substantially concave proximal surface and a hole extending into the center of the proximal surface, the hole being adapted to receive a plunger pin carried on a patient's residual limb therein;
a lock positioned within the housing for securing the plunger pin received in the hole; and
means for securing the housing within a prosthetic limb socket;

the housing being substantially cylindrical and the concave proximal surface including a plurality of radially extending grooves, each groove having a concave elevational cross-section.

25. The shuttle-lock of claim 24, wherein the cross-section is uniform in the radial direction.

26. A shuttle-lock for maintaining a patient's residual limb in a prosthetic limb socket, the shuttle-lock comprising:

a housing having a distal surface adapted to abut an inside surface of a prosthetic limb socket, a substantially concave proximal surface and a hole extending into the center of the proximal surface, the hole being adapted to receive a plunger pin carried on a patient's residual limb therein;

a lock positioned within the housing for securing the plunger pin received in the hole; and means for securing the housing within a prosthetic limb socket;

the housing being substantially cylindrical and the concave proximal surface including a plurality of radially extending grooves, each groove being circumferentially distributed about the hole and providing an unobstructed path for the plunger pin to be received within a groove of the plurality of radially extending grooves and guided directly into the hole.

* * * * *

UNITED STATES PATENT AND TRADEMARK OFFICE
CERTIFICATE OF CORRECTION

PATENT NO. : 6,689,171 B2  Page 1 of 1
APPLICATION NO. : 10/103901
DATED : February 10, 2004
INVENTOR(S) : Tracy C. Slemker, Scott R. Schall and Steve Steinbarger It is certified that error appears in the above-identified patent and that said Letters Patent is hereby corrected as shown below:

Column 8, line 22, "ping" should be changed to --pin--.
Column 12, lines 12, 19, and 25, "distal" should be changed to --proximal--.

Signed and Sealed this

Thirty-first Day of March, 2009

JOHN DOLL
*Acting Director of the United States Patent and Trademark Office*